US007204825B2

(12) United States Patent
Cimino et al.

(10) Patent No.: US 7,204,825 B2
(45) Date of Patent: *Apr. 17, 2007

(54) SURGICAL SYSTEM CONSOLE

(75) Inventors: William Wayne Cimino, Louisville, CO (US); Kristen Marie Morahan, Louisville, CO (US); Robert Lewis Blythe, Longmont, CO (US)

(73) Assignee: Integra LifeSciences (Ireland) Ltd., Dublin (IE)

( * ) Notice: Subject to any disclaimer, the term of this patent is extended or adjusted under 35 U.S.C. 154(b) by 225 days.

This patent is subject to a terminal disclaimer.

(21) Appl. No.: 10/628,673

(22) Filed: Jul. 28, 2003

(65) Prior Publication Data

US 2004/0068208 A1 Apr. 8, 2004

Related U.S. Application Data

(63) Continuation of application No. 09/396,903, filed on Sep. 15, 1999, now Pat. No. 6,602,227.

(60) Provisional application No. 60/101,801, filed on Sep. 25, 1998.

(51) Int. Cl.
*A61F 7/12* (2006.01)
(52) U.S. Cl. .................................................. 604/113
(58) Field of Classification Search ............ 604/19, 604/22, 27, 35, 43, 65, 67, 73, 93.01, 113, 604/246, 259; 606/107, 169, 170, 171
See application file for complete search history.

(56) References Cited

U.S. PATENT DOCUMENTS

| | | | |
|---|---|---|---|
| 4,768,496 A | 9/1988 | Kreizman et al. | ........ 123/24 A |
| 4,915,639 A | 4/1990 | Cohn et al. | |
| 4,983,160 A | 1/1991 | Steppe et al. | |
| 5,197,895 A | 3/1993 | Stupecky | |
| 5,413,574 A | 5/1995 | Fugo | ........................... 128/898 |
| 5,491,418 A | 2/1996 | Alfaro et al. | |
| 5,606,345 A | 2/1997 | Truchet | |
| 5,616,120 A * | 4/1997 | Andrew et al. | ................ 604/28 |
| 5,708,460 A | 1/1998 | Young et al. | |
| 5,885,243 A | 3/1999 | Capetan et al. | |
| 6,117,126 A * | 9/2000 | Appelbaum et al. | ........... 606/1 |
| 6,602,227 B1 * | 8/2003 | Cimino et al. | .............. 604/113 |

OTHER PUBLICATIONS

"Third Party Review Guidance For Phacofragmentation System Device Premarket Notification (510(k))", Department of Health and Human Services, Food and Drug Administration, Center for Devices and Radiological Health, Jan. 21, 1997.

* cited by examiner

*Primary Examiner*—Catherine S. Williams
(74) *Attorney, Agent, or Firm*—Fulwider Patton LLP

(57) ABSTRACT

An improved surgical console for use with a handheld tissue fragmentation device includes portable base having an upper portion. An adjustable display head is mounted to the upper portion of the base. The display head provides rotational and translational adjustment relative to the base. An aspiration system is coupled to the fragmentation device for aspirating fluid and tissue fragmented by the fragmentation device from a surgical site. An irrigation system is also coupled to the fragmentation device for supplying irrigating fluid to the surgical site for suspending tissue fragmented by the fragmentation device. A power system is coupled to the fragmentation device for energizing a transducer of the fragmentation device for fragmenting tissue.

22 Claims, 4 Drawing Sheets

FIG_1

FIG_2

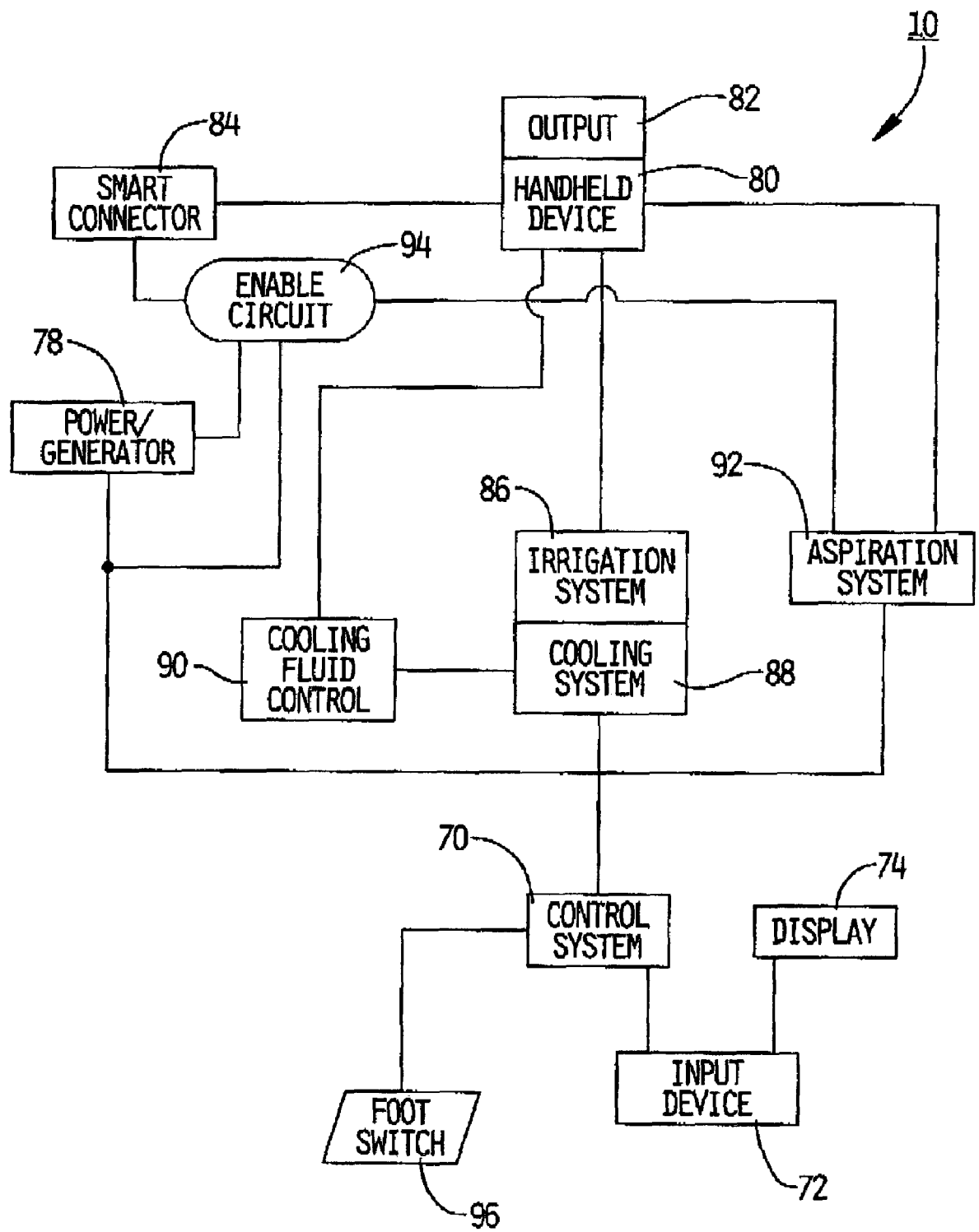

SURGICAL SYSTEM CONSOLE

This application is a continuation of U.S. application Ser. No. 09/396,903, filed Sep. 15, 1999, now U.S. Pat. No. 6,602,227, which claims priority from provisional application Ser. No. 60/101,801, filed Sep. 25, 1998.

BACKGROUND

1. Technical Field

This disclosure relates to ultrasound surgical systems and, more particularly to an improved ultrasonic surgical system console.

2. Background of Related Art

Devices which effectively utilize ultrasonic energy for a variety of applications are well-known in a number of diverse arts. The application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become well-known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having a substantially constant amplitude at a predetermined frequency (i.e. 20–30 kHz). Certain limitations have emerged in attempts to use such devices in a broad spectrum of surgical procedures. For example, the action of a continuously vibrating tip does not have a desired effect in breaking up certain types of body tissue, bone, etc. Because the ultrasonic frequency is limited by the physical characteristics of the handheld device, only the motion available at the tip provides the needed motion to break up a particular tissue. The limited focus of a device is ineffective for certain applications due to the vibrations which may be provided by the handheld device. For certain medical procedures, it may be necessary to use multiple hand held devices or it may be necessary to use the same console for powering different handheld devices.

Therefore, a need exists for an ultrasonic console which may be used with handheld devices which operate at different frequencies. A further need exists for a console which has connectors from the handheld device which identify the device to ensure the appropriate device is chosen.

Ultrasonic consoles provide aspiration through vacuum lines coupled to the handheld device. Ultrasonic vibration is provided by activating an actuation element. Conventionally actuating elements are provided with power through a power switch, usually a foot switch. These systems typically break the aspirating vacuum when the ultrasonics are turned off.

Therefore, a need exists for an ultrasonic console which provides for separate switching between the aspiration vacuum and the ultrasonics circuitry. A further need exists for a surgical apparatus which provides increased ease of use.

SUMMARY

An improved surgical console for use with a handheld tissue fragmentation device includes a portable base having an upper portion. An adjustable display head is mounted to the upper portion of the base. The display head provides rotational and translational adjustment relative to the base. An aspiration system is coupled to the fragmentation device for aspirating fluid and tissue fragmented by the fragmentation device from a surgical site. An irrigation system is also coupled to the fragmentation device for supplying irrigating fluid to the surgical site for suspending tissue fragmented by the fragmentation device. A power system is coupled to the fragmentation device for energizing a transducer of the fragmentation device for fragmenting tissue. The aspiration system may include a tissue receptacle for receiving fragmented tissue from the surgical site. The irrigation system may include a user supplied reservoir for storing the irrigating fluid therein. A control system is also included for controlling and coordinating the power system, the aspiration system and the irrigation system during a surgical procedure.

In alternate embodiments of the surgical consoles and surgical systems as described, the fragmentation device preferably includes a cable having a terminal for connecting to the power system. The terminal may include a connector pattern for identifying the fragmentation device to the console, or the fragmentation device has a memory, the memory for storing data and identifying the fragmentation device to the console when coupled to the console. A cooling system may also be included for cooling the fragmentation device. A fluid control device is provided for monitoring cooling fluid pressure levels. A system for filling and draining the cooling fluid levels from the fragmentation device may also be included. The display head may include a touchscreen input. The power system may include a tissue release function such that power to a tissue release valve is turned off momentarily. The power system may include a laparoscopic function such that power to the tissue release valve and aspiration is turned on only during fragmentation.

These and other objects, features and advantages of the present disclosure will become apparent from the following detailed description of illustrative embodiments thereof, which is to be read in connection with the accompanying drawings.

BRIEF DESCRIPTION OF THE DRAWINGS

Various embodiments are described herein with reference to the drawings, wherein:

FIG. 5 is a block/schematic diagram of the console of FIG. 1 showing various systems and components.

DETAILED DESCRIPTION OF PREFERRED EMBODIMENTS

The present disclosure describes an improved apparatus for the fragmentation and removal of tissue, preferably for ultrasonic applications. A surgical system console includes an adjustable head having a display mounted thereon. The adjustable head provides for vertical and rotational adjustment to provide greater flexibility and ease of use. The display preferably includes a touchscreen architecture such that operators way issue cords and control the console by simply touching preselected features displayed in designated fields on the display. The display may further include display controls for adjusting image quality. The console further includes sockets for receiving plugs of various handheld devices used for surgery. The console utilizes smart connectors which can identify the handheld device to be used, select appropriate settings for the handheld device and provide data about the particular handheld device.

The console is equipped with, among other things, an irrigation reservoir and a tissue collection volume. The console provides vacuum or, alternatively may provide hook-up to an institution's vacuum ports. The console advantageously includes a tissue release function which temporarily suction. Further, the console provides an automatically controlled fill and drain system for providing cooling fluid to the handheld device. The cooling fluid is preferably distilled water while the irrigation fluid is a sterile saline solution.

An enhanced laparoscopic feature is also included wherein suction from the vacuum is interrupted unless the handheld device is activated. For example, during ultrasonic laparoscopic surgery, suction is off when fragmentation is activated. This advantageously prevents loss of pneumoperitoneum during surgery.

Figure 1:
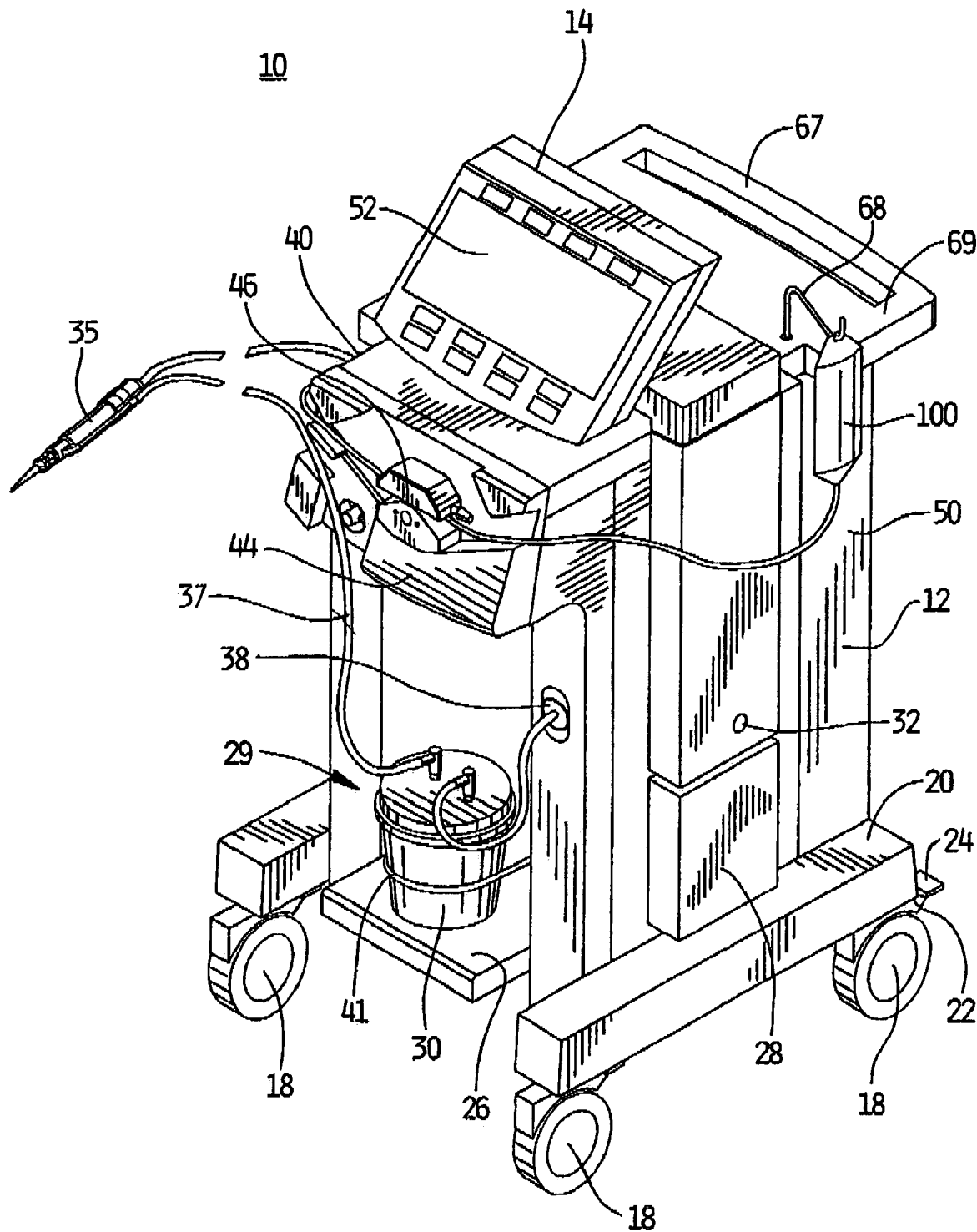
FIG. 1 is a perspective view of one embodiment of a surgical console constructed in accordance with the present disclosure.

Referring now in specific detail to the drawings in which like reference numerals identify similar or identical elements throughout the several views, and initially to FIG. 1, one embodiment of a surgical system console is shown generally as console 10. Console 10 includes a base 12 which supports an adjustable head 14. Base 12 includes wheels or casters 18 which mount to a lower portion 20 of base 12 and render console 10 portable. Wheels 18 are preferably mounted in a bearing or housing which permits rotation of wheels 18 to provide steering capability and provide additional flexibility and convenience to an operator. Wheels 18 may further include a locking mechanism 22 to prevent motion of wheels 18 relative to a support surface, such as a floor. Locking mechanism 22 preferably includes a lever 24 which may be positioned to release or lock wheels 18 in place. Lever 24 may be foot activated to adjust between the locked and the released positions.

Base 12 provides structure 26 for supporting a tissue receptacle 30. Structure 26 include opening 29 dimensioned and configured for receiving reservoir 30. Irrigation reservoir 28 is coupled to a release button 32. Intake and output interfaces are internal. Irrigation fluid prevents coagulation of blood and provides cooling fluid to the tip.

Receptacle 30 is coupled to a vacuum port 38 through a filter (not shown). Vacuum source may be included in console 10 or be supplied from an external source. Receptacle 30 is further connected to a vacuum port 38 a communicates therewith to retrieve fragmented tissue provided by the operation of handheld device at a surgical site. Collection receptacle 30 connects to handheld device 35 by a vacuum tube 37 to provide aspiration at the surgical site. Also included are restraints 41 for supporting receptacle 30.

A connector receptacle 40 is included on console 10. Connector receptacle 40 provides an interface between handheld device 35 and the console to provide power to the fragmentation system, for example, power to actuate a transducer (not shown) in handheld device 35. The transducer has, for example, magnetostrictive or piezoelectric elements in the handheld device, which are supplied power through connector receptacle 40.

Figure 2:
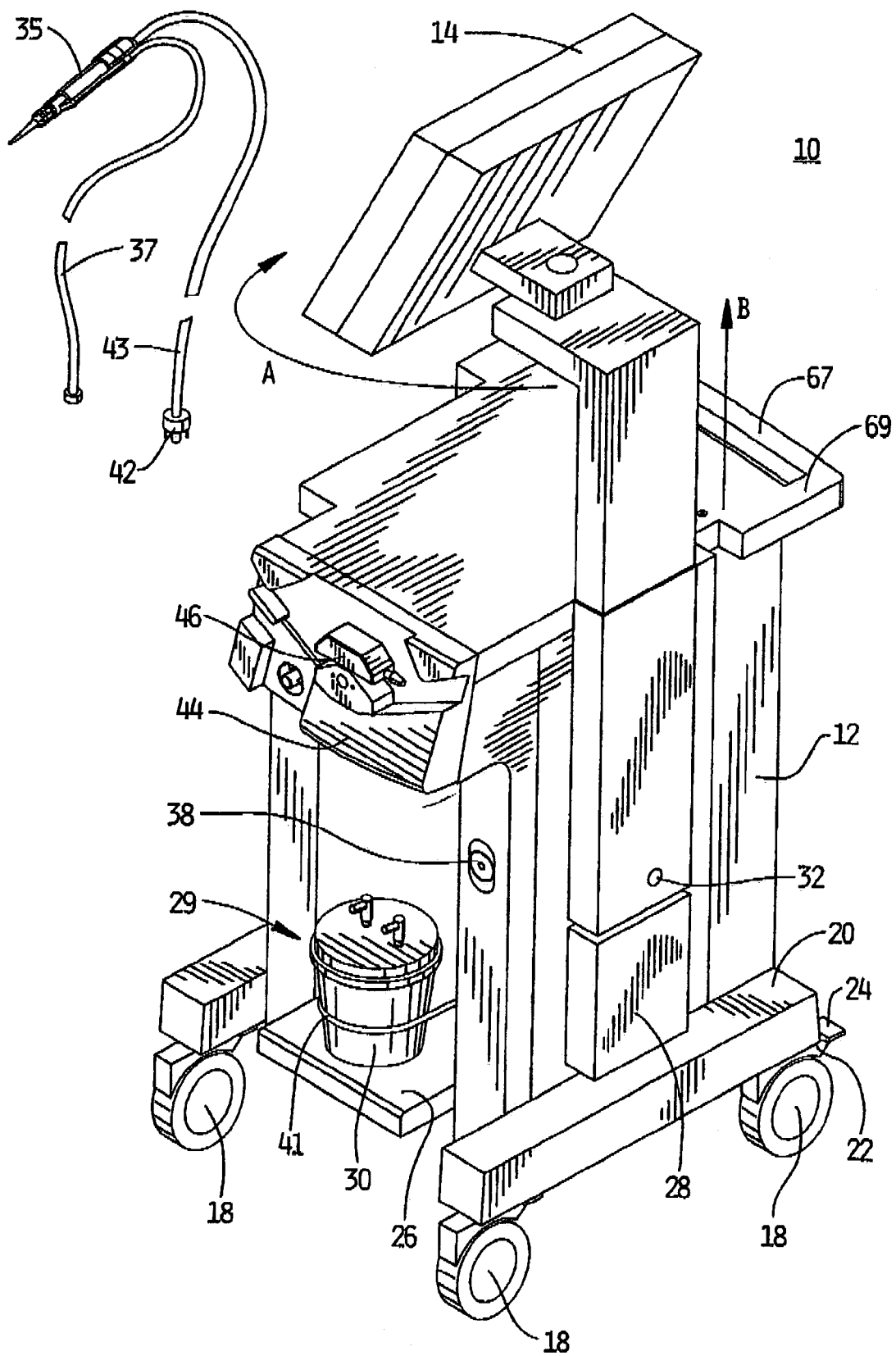
FIG. 2 is a perspective view of the surgical console of FIG. 1 showing adjustability of a head on the console.

Referring to FIG. 2, handheld device includes a cable 43 terminating in a plug 42 which engages and connects with receptacle 40 in a male/female relationship. Interface connections between plug 42 and receptacle 40 are preferably smart connections. That is, handheld device 35 is identified to console 10 by merely plugging it into console 10. This feature may be realized by designing specific plug/receptacle pattern which are unique 10 certain handheld devices. Further, smart connectors may be realized by memory storage within each handpiece which is activated upon connection to console 10. Memory storage identifies the handheld device and may also provide pertinent data about the device or give instructions which may be displayed by console 10. Smart connections similar to those described in U.S. Pat. No. 5,491,418 to Alfaro, et al., U.S. Pat. No. 5,197,895 to Stupecky and U.S. Pat. No. 4,915,639 to Cohn et al. all incorporated herein by reference, may be used.

A surface 44 extend outward from console 10. Surface 44 includes recessed surfaces and extended surfaces for aspiration and irrigation tube routing. Extended surface 69 provides an operator location to store the handpiece. An irrigation pump 46 supplies irrigation for the surgical handpiece.

Referring to FIG. 2, adjustable head 14 adjustably mounts to an upper portion 50 of base 12. Adjustable head 14 includes a display 52 (FIG. 1) thereon. Head 14 is adjustable and provides several degrees of freedom. Head 14 is angled at about 45° and swivels in the direction of arrow "A", and telescopes in the direction of arrow "B". Head 14 is advantageously designed to reach eye-level, for example, display 52 (FIG. 1) of head 14 may be located from between 40 inches to about 52 inches in height from the support surface, for example the floor. Head 14 translates in the direction of arrow "B" in case additional height is desired. Once extended, swiveled or rotated, head 14 may be secured in place by devices known to those skilled in the art such as by thumb screws, ratchets, etc.

A height adjustable intravenous (I.V.) pole and hook 68 may be included for the convenience of the operators or surgeons. Further, extensions 69 and a crossbar 67 may be provided for use as a handle for pushing or maneuvering console 10.

Figure 3:
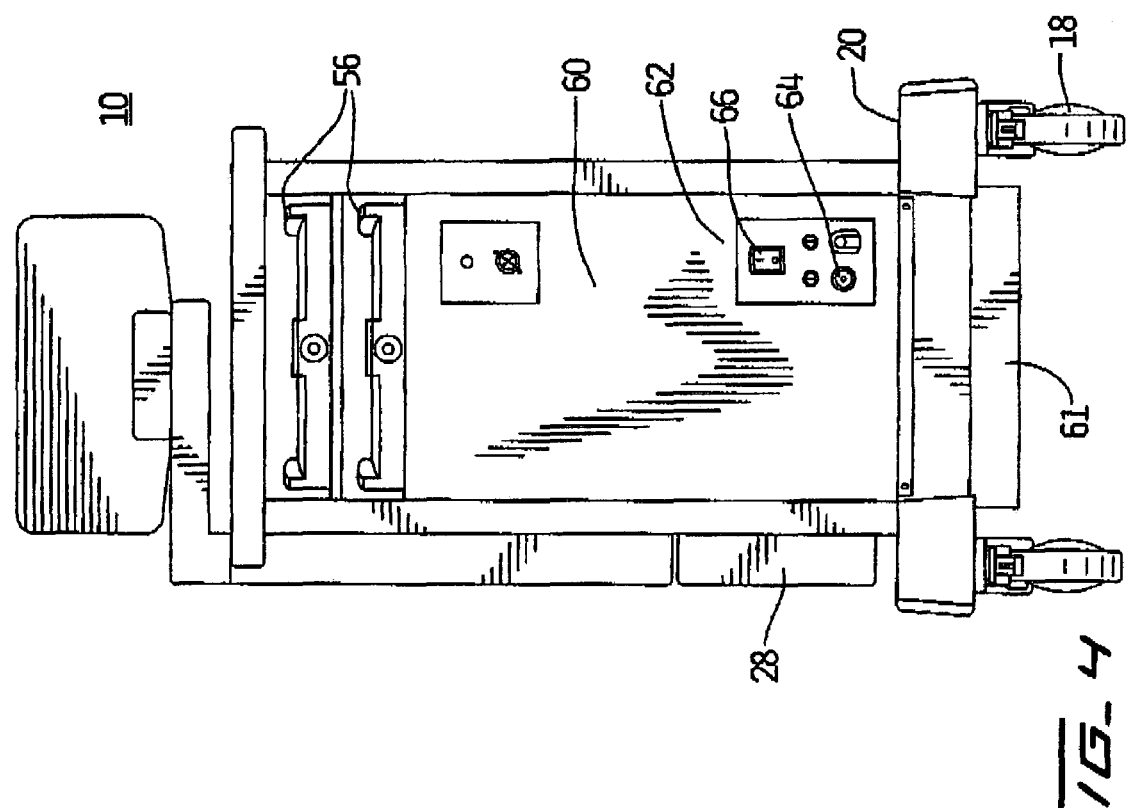
FIG. 3 is a front view of the surgical console of FIG. 1.

Referring to FIG. 3, display 52 is preferably a touchscreen display. Touch screen displays are described in U.S. Pat. No. 5,606,345 to Truchet and. U.S. Pat. No. 5,708,460 to Young et al. both incorporated herein by reference. Interactions between operator and console i0 may be performed by issuing commands on touch sensitive areas 51 of display 52. In this way, an easier, more user friendly interface is achieved. Display 52 also includes controls or buttons 54 for activating and initiating console and display functions. Console 10 includes memory for storing software for executing various commands and functions for the appropriate operation of console 10 and the handheld device during surgery. A system power switch 53 is also located on the front portion of base 12.

Figure 4:
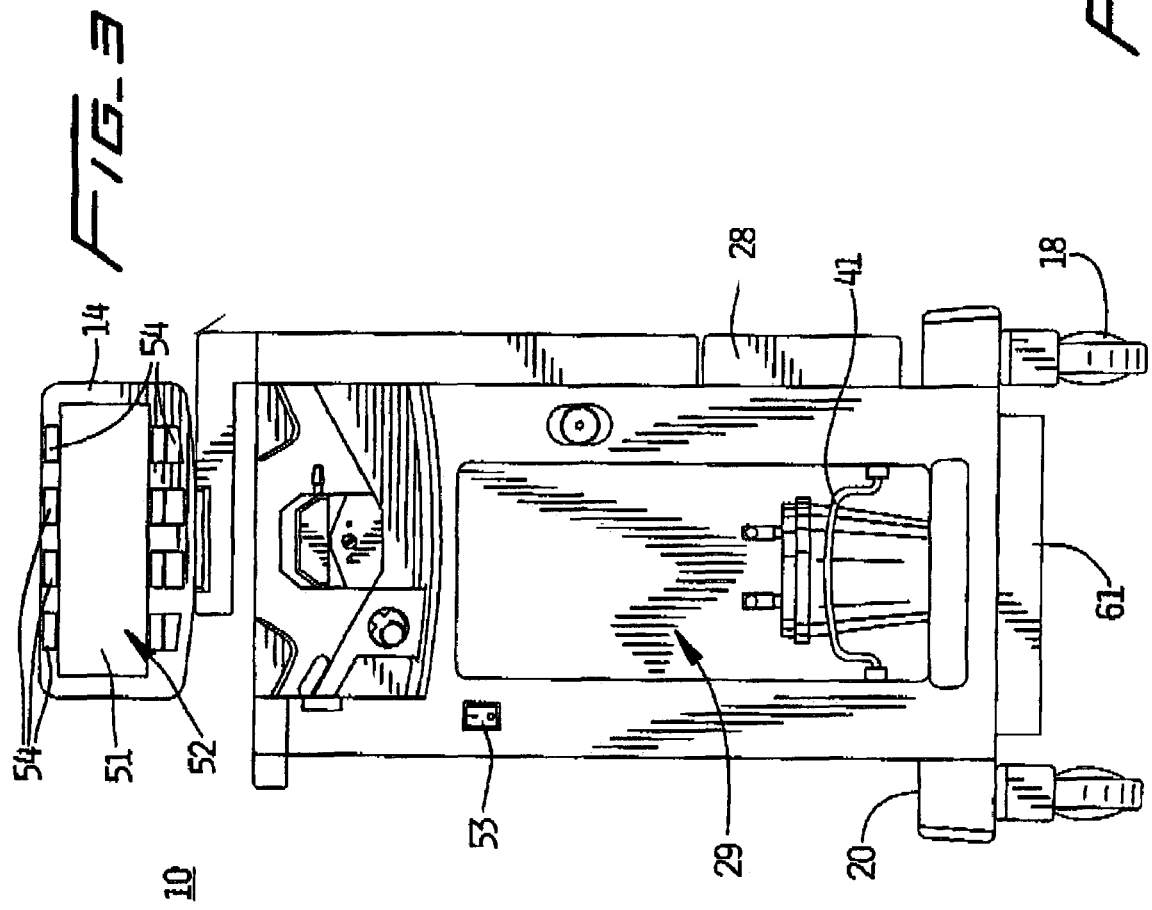
FIG. 4 is a rear view of the surgical console of FIG. 1.

Referring to FIG. 4, a rear panel 60 of console 10 is shown. Upper portion 50 of base 12 includes compartments 56 for storage of, for example manuals, cables and tubes for use with the various functions of console 10. A storage compartment 61 is provided at the bottom of the console for e.g. footswitches. A power interface 62 is included for providing electrical power to console 10. A equipotential ground plug 64 is included with an AC main switch 66. During a surgical procedure, it may be desirable to use vacuum suction from an external source.

Referring to FIG. 5, block/schematic diagram of console 10 is shown. Console 10 includes a control system 70 which preferably includes a processor and memory for storage of software applications for controlling the various system functions maintained during use. Control system 70 may further include logic circuitry for activating alarms, system checks, etc. Input from an operator is provided by input device 72. Input device 72 may included designated buttons, including virtual buttons, such as those associated with touchscreen displays. Other inputs devices way include knobs, a keypad, voice activation, etc. A display 74 as described in detail above is included for visually displaying data and providing user friendly control of console 10.

Control system 70 oversees operation of three main systems of console 10. A power system 78 provides power to a handheld device 80 used for surgery. Handheld device 80 may by used to perform surgery in a multiplicity of different ways. For example, handheld device 80 may provide ultrasonic vibrations for ultrasonic fragmentation of tissue at an operative site, further handheld device may provide RF electrical current to al operative site for electrosurgery. In a preferred embodiment, handheld device 80 is used for ultrasonic surgery. Power system 78 provides an alternating signal to a transducer located in handheld device 80 thereby causing a standing ultrasonic wave in device 80. Device 80 includes an output 82 which provides the fragmenting action for breaking down tissue. For ultrasonics, output 82 includes a vibrating tip. Power system 78 includes a frequency generator which supplies an electrical s6 at a desired frequency to the transducer. Power system 78 is coupled to handheld device 80 by a smart connector 84. Smart connector 84 is described hereinabove.

An irrigation system 86 is included and controlled by control system 70. Irrigation system 86 provides several functions. One such function provides fluid to an operative site to assist in preventing coagulation of blood in vacuum hoses. This fluid is maintained and circulated from user supplied bag 100 (FIG. 1). A cooling system is provided to supply cooling fluid to handheld device 80 by flowing through flues in handheld device 80 thereby removing heat from active elements of device 80. Cooling system 88 is automatically filled and drained as needed. The automatic control is provided by cooling fluid control device 90. Device 90 preferably includes circuitry for measuring and comparing fluid pressure levels.

An aspiration system 92 is included and is controlled by control system 70. Aspiration system 92 removes tissue and fluids from the operative site through handheld device 80 during surgery.

Aspiration system 92 and power system 78 are coupled by an enable circuit 94. Enable circuit 94 provides a tissue release function. Power from power system 78 is stopped to halt fragmentation (as indicated by control system) while continuing suction from aspiration system 92. Advantageously, an operator may continue to remove tissue from an operative site without continuing to fragment tissue.

A laparscopic feature is also included and implemented using enable circuit 94. Enable circuit 94 disables suction form aspiration system 92 unless power system 78 is activating handheld device 80. This feature advantageously prevents loss of pneumoperitoneum during laparoscopic surgery.

Enabling circuit 94 preferably includes logic circuitry (i.e. AND/OR gates) which enables power and signal when appropriate inputs are present. For example with the laparoscopic feature, if the ultrasonics of handheld device 35 is activated, a signal is sent to the aspiration system thereby enabling the aspiration system to supply vacuum. Similarly for the tissue release feature, when the power to the ultrasonics is disabled, vacuum is maintained by aspiration system by power supplied through the circuitry of enable circuit 94.

Other features of console 10 include a foot switch 96 for enabling one or more of the systems described hereinabove.

It is also contemplated that the console 10 be configured wit a quiet state noise reduction mode. This mode will temporarily deactivate one or more of the higher decibel systems of the console, such as, e.g. the suction system, based on predetermined conditions. For example, if the surgeon has not keyed the ultrasonics on for a predetermined time period, e.g. 2–10 minutes, the console will temporarily go into the noise reduction mode by deactivating the suction system. This mode substantially enhances the operating room conditions by quieting unnecessary noise.

It will be understood that various modifications may be made to the embodiments disclosed herein. For example, other mechanisms may be used to allow adjustability of head 14 such as a spring loaded linkage for assisting in moving and maintaining the head in the desired position. Further, screen text may be displayed in various languages to provide additional convenience to operators. Therefore, the above description should not be construed as limiting, but merely as exemplifications of preferred embodiments. Those skilled in the art will envision other modifications within the scope and spirit of the claims appended hereto.

What is claimed is:

1. An Improved surgical console for use with a handheld tissue fragmentation device comprising:
   a portable base having an upper portion;
   an adjustable display head mounted to the upper portion of the base, the display head providing rotational and translational adjustment relative to the base;
   an aspiration system for coupling to a fragmentation device for aspirating fluid and tissue fragmented by the fragmentation device from a surgical site;
   a cooling system adapted for circulating a cooling liquid to the fragmentation device, the cooling system being separate from the aspiration system and irrigation system;
   an irrigation system for coupling to the fragmentation device for supplying irrigating fluid to the surgical site for suspending tissue fragmented by the fragmentation device; and
   a power system for coupling to the fragmentation device for energizing a transducer of the fragmentation device for fragmenting tissue.

2. The surgical console as recited in claim 1, further comprises a fragmentation device which includes a cable having a terminal for connecting to the power system.

3. The surgical console as recited in claim 2, wherein the terminal includes a connector pattern for identifying the fragmentation device to the console.

4. The surgical console as recited in claim 2, wherein the fragmentation device has a memory, the memory for storing data and identifying the fragmentation device to the console when coupled to the console.

5. The surgical console as recited in claim 1, further comprising a fluid control device for monitoring cooling fluid levels and automatically filling and draining the cooling liquid in response to feedback from the fragmentation device.

6. The surgical console as recited in claim 1, wherein the display head includes touchscreen input.

7. The surgical console as recited in claim 1, wherein the power system includes a tissue release function such that aspiration is turned off while maintaining power to a transducer of a fragmentation device.

8. The surgical console as recited in claim 1, wherein the power system includes a laparoscopic function such that aspiration is activated only when the ultrasonics are activated.

9. An improved surgical console for ultrasonic fragmentation surgery for use with a handheld tissue fragmentation device comprising:
   a portable base having an upper portion, the base forming support structures therein;
   an adjustable display head mounted to the upper portion of the base, the display head providing rotational and translational adjustment relative to the base;
   an aspiration system for coupling to the fragmentation device for aspirating fluid and tissue fragmented by the fragmentation device from a surgical site, the aspiration system including a tissue receptacle for receiving fragmented tissue from the surgical site;
   a cooling system connected to the surgical device and configured to circulate a cooling fluid for cooling the surgical device;
   a cooling fluid control device having means for monitoring cooling fluid levels and automatically filling and draining the cooling fluid in response to at least one feedback signal from the surgical device;
   an irrigation system for coupling to the fragmentation device for supplying irrigating fluid to the surgical site for suspending tissue fragmented by the fragmentation device, the irrigation system including a reservoir for storing the irrigating fluid therein; and
   a power system for energizing an ultrasonic transducer of the fragmentation device for ultrasonically fragmenting tissue.

10. The surgical console as recited in claim 9, further comprising a detachable fragmentation device including a cable having a terminal for connecting to the power system.

11. The surgical console as recited in claim 10, wherein the terminal includes a connector pattern for identifying the fragmentation device to the console.

12. The surgical console as recited in claim 10, wherein the fragmentation device has a memory, the memory for storing data and identifying the fragmentation device to the console when coupled to the console.

13. The surgical console as recited in claim 9, wherein the display head includes touch screen input.

14. The surgical console as recited in claim 9, wherein the power system includes a tissue release function such that power to a traducer of a fragmentation device is turned off while maintaining aspiration.

15. The surgical console as recited in claim 9, wherein the power system includes a laparoscopic function such that power to a transducer of a fragmentation device is turned on only while maintaining aspiration.

16. A surgical system for fragmentation of tissue comprising:
   a portable base having an upper portion;
   an ultrasonic tissue fragmentation device coupled to the base;
   an adjustable display head mounted to the upper portion of the base, the display head providing rotational and translational adjustment relative to the base, the display head for providing data and permitting input from an operator on a display screen disposed thereon;
   an aspiration system coupled to the fragmentation device for aspirating fluid and tissue fragmented by the fragmentation device from a surgical site;
   an irrigation system coupled to the fragmentation device for supplying irrigating fluid to the surgical site for suspending tissue fragmented by the fragmentation device;
   a cooling system configured solely for cooling the fragmentation device, the cooling system configured for circulating a cooling liquid and including an automatic control device, wherein the automatic control device monitors cooling fluid levels and drains the cooling fluid in response to feedback from the fragmentation device;
   a power system coupled to the fragmentation device for energizing an ultrasonic transducer of the fragmentation device for fragmenting tissue by supplying ultrasonic vibrations to a fragmentation tip, the power system including a frequency generator for generating output frequencies to the transducer; and
   a control system for controlling and coordinating the power system, the aspiration system and the irrigation system during a surgical procedure.

17. The surgical console as recited in claim 16, wherein the fragmentation device includes a cable having a terminal for connecting to the power system.

18. The surgical system as recited in claim 17, wherein the terminal includes a connector pattern for identifying the fragmentation device to the console.

19. The surgical system as recited in claim 17, wherein the fragmentation device has a memory, the memory for storing data and identifying the fragmentation device to the console when coupled to the console.

20. The surgical system as recited in claim 16, wherein the display head includes touch screen input.

21. The surgical system as recited in claim 16, wherein the power system includes a tissue release function such that aspiration is turned off while maintaining power to the transducer.

22. The surgical system as recited in claim 16, wherein the power system includes a laparoscopic function such that aspiration is activated only when the ultrasonics are activated.

* * * * *